United States Patent

Marcus et al.

[11] Patent Number: 5,842,387
[45] Date of Patent: *Dec. 1, 1998

[54] KNIFE BLADES HAVING ULTRA-SHARP CUTTING EDGES AND METHODS OF FABRICATION

[76] Inventors: Robert B. Marcus, 133 Colchester Rd., Murray Hill, N.J. 07974; William Stuart Trimmer, 58 Riverview Ter., Belle Mead, N.J. 08502

[*] Notice: The terminal 7 months of this patent has been disclaimed.

[21] Appl. No.: 335,260

[22] Filed: Nov. 7, 1994

[51] Int. Cl.$^6$ ................................................. B21K 11/00
[52] U.S. Cl. .................. 76/104.1; 76/DIG. 6; 76/DIG. 8
[58] Field of Search .............................. 76/104.1, 107.1, 76/DIG. 8, DIG. 6; 30/350, 346.54, 355

[56] References Cited

U.S. PATENT DOCUMENTS

| | | | |
|---|---|---|---|
| 4,210,041 | 7/1980 | Mitman et al. | 76/107.1 |
| 4,579,022 | 4/1986 | Kasai et al. | 76/107.1 |
| 4,671,849 | 6/1987 | Chen et al. | 156/643 |
| 4,916,002 | 4/1990 | Carver | 428/139 |
| 5,142,785 | 9/1992 | Grewal et al. | 76/DIG. 8 |
| 5,201,992 | 4/1993 | Marcus et al. | 156/643 |
| 5,204,581 | 4/1993 | Andreadakis et al. | 313/336 |
| 5,261,922 | 11/1993 | Hood | 30/355 |
| 5,266,530 | 11/1993 | Bagley et al. | 437/228 |
| 5,317,938 | 6/1994 | de Juan, Jr. et al. | 76/104.1 |

FOREIGN PATENT DOCUMENTS

| | | | |
|---|---|---|---|
| 56-3152 | 1/1981 | Japan | 30/350 |
| 57-28637 | 2/1982 | Japan | 76/107.1 |

Primary Examiner—Rinaldi I. Rada
Assistant Examiner—Charles Goodman
Attorney, Agent, or Firm—Michael Y. Epstein

[57] ABSTRACT

Knife blades having exceptionally sharp cutting edges are formed from wafers of monocrystalline silicon using known semiconductor processing technology. In one embodiment, an elongated ridge having a flat top covered by an etchant mask is etched to undercut the mask and to shape the ridge side walls to inwardly converge towards the ridge tip. The mask is removed and a sharp ridge apex is provided by a series of oxide forming and oxide stripping processes. Individual knife blades of silicon, each comprising a ridge having a sharp cutting edge, are shaped from the wafer. In another embodiment, the silicon wafer is etched entirely through between top and bottom surfaces to form a tapered etched wall intersecting the bottom wall at a highly acute edge. The edge is sharpened by the oxide forming and oxide stripping process to form a cutting edge in the completed blade. In both embodiments, various etch masks and etching procedures are used for providing blades of various shapes.

10 Claims, 18 Drawing Sheets

KNIFE BLADES HAVING ULTRA-SHARP CUTTING EDGES AND METHODS OF FABRICATION

BACKGROUND OF THE INVENTION

This invention relates to implements, particularly knife blades, having ultra sharp cutting edges formed from semiconductor materials, preferably monocrystalline silicon. By "ultra-sharp" is meant that the radius of curvature of the cutting edges can be as small as 0.5 nm while extending up to 100 nm. As such, the edges can be "atomically" sharp. Often, however, for reasons of strength and durability, somewhat less sharp edges are preferred.

Examples of semiconductor processes relevant to the present invention are disclosed in U.S. Pat. Nos. 5,100,355, 5,201,992, 5,204,581 and 5,266,530, the subject matter of which is incorporated herein by reference. These patents, in connection with the fabrication of various electrical devices, e.g., electron "point" emitters, disclose the formation of silicon needles or cones by selective etching processes and the sharpening of the needle points by an oxidizing and oxide stripping process performed one or more times dependent upon the degree of sharpening desired.

These patents make no disclosure or suggestion of cutting implements such as knife blades, and make only passing reference to elongated ridges having sharp apices. Also, the structures described in the patents are not suited for use as cutting edges in cutting implements.

SUMMARY OF THE INVENTION

The invention resides, in part, in the recognition that the technology shown in the above cited patents is useful in the fabrication of implements having cutting edges, and disclosed hereinafter are various novel and inventive variations and applications of technology for fabricating cutting and/or slicing instruments having edges of exceptional sharpness.

In accordance with one aspect of the invention, an elongated ridge having a very sharp apex is formed extending along a surface of a block of silicon. Preferably, the silicon block is part of a wafer of silicon having a flat surface, and a plurality of ridges are provided on the flat surface. Also, one side wall of each ridge preferably rises from a wafer first flat surface while the opposite side wall rises from a wafer second flat surface vertically spaced from the first surface; the height of the ridges thus varying from side to side thereof with respect to the adjoining wafer surfaces. Then, for forming structures suitable for use as cutting implements, e.g., for use as microtome knives or surgical scalpels, deep trenches or grooves are formed in the wafer extending downwardly from the flat surface or surfaces and entirely through the thickness of the wafer.

Pairs of trenches are disposed adjacent and parallel to opposite sides of each of the elongated ridges, with at least one trench of each pair so close to the ridge that a side wall of the one trench effectively forms an extension of an adjoining side wall of the ridge. Small, generally rectangular blocks of silicon, each containing a single extending ridge, are then separated from the wafer. Each block comprises a knife blade having a cutting edge disposed at the intersection of two block side surfaces. One surface comprises the wafer flat surface adjoining one side of the ridge, and the other surface is the side wall of the one trench adjoining the opposite side of the ridge.

In accordance with a second aspect of the invention, a silicon block having oppositely disposed first and second surfaces is etched entirely through from the first to the second surface. By use of various surface masking and etching techniques described hereinafter, the etched surface is caused to intercept the second surface at a highly acute angle for forming what is to be a blade edge disposed between the etched surface and the second surface. Additionally, the shape of the etched surface is controlled for providing blades having various desirable side surface configurations.

Depending upon the eventual use of the blades, the blade edges can be sharpened to practically "atomic sharpness". Preferably, however, for reasons of strength and durability, the blade edges and/or edge adjoining surfaces are coated with a protective coating, e.g., silicon dioxide, silicon nitride and/or various smooth and hard materials commonly used to coat knife blades. Such coatings, if used, reduce the sharpness of the edges, but exceptionally sharp edges are still provided.

DESCRIPTION OF THE DRAWINGS

The various figures are schematic and not drawn to scale.

FIG. 15 (previously referred to) is a cross-section of the blade workpiece taken along line 16—16 of FIG. 14;

FIG. 22 is a view similar to FIG. 21 but showing a variation therefrom;

FIGS. 46–53 are various sectional views and FIG. 54 is a perspective view illustrating variations from processing steps illustrated in previously described figures.

DESCRIPTION OF PREFERRED EMBODIMENTS OF THE INVENTION

Figure 1:
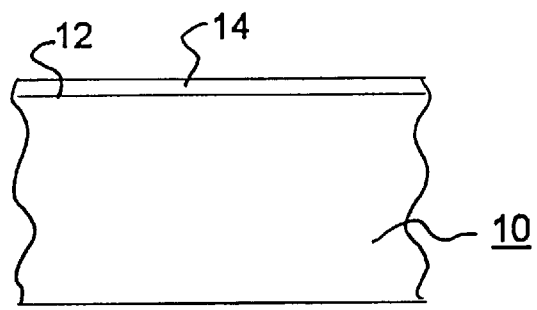
FIGS. 1, 2, 4, 5, 8–13, 15, 17, 21 and 22 are a series of cross-sectional views of a semiconductor workpiece illustrating a sequence of processing steps in accordance with one aspect of the invention for forming a knife blade.

The starting workpiece (FIG. 1 herein) comprises a monocrystalline silicon substrate 10, referred to as a "wafer", having a surface 12 lying in a {110} crystalline plane. As is common in the semiconductor device art, a relatively large wafer is used and a plurality of identical devices are simultaneously fabricated on the wafer. In a final process, the individual devices are separated from one another. In the following, the fabrication of but one device of many on the wafer is described.

Figure 2:
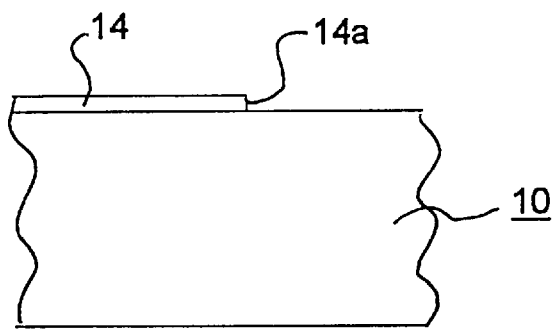
Figure 3:
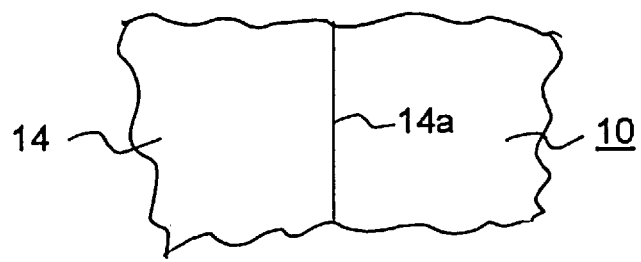
FIGS. 3 and 6 are plan views of the workpiece shown in FIGS. 2 and 5, respectively.
Figure 4:
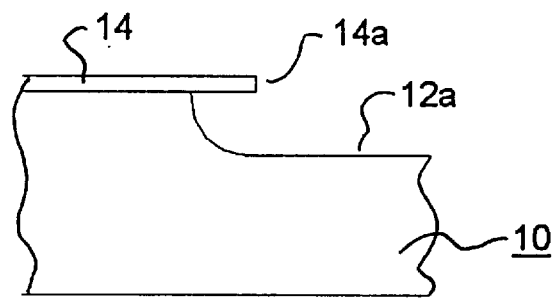
Figure 44:
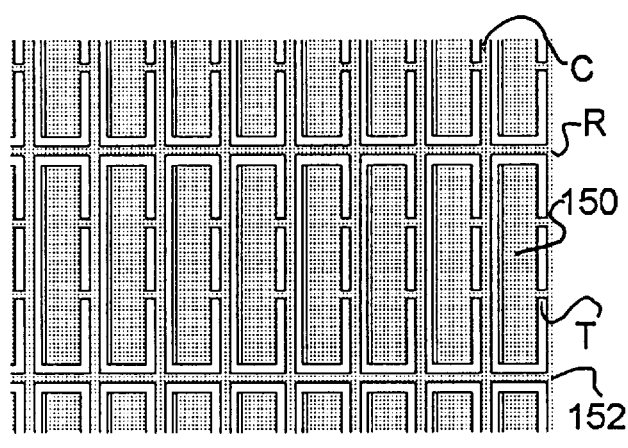
FIGS. 44 and 45 are plan views each showing a portion of a wafer of the type used in the semiconductor device industry and used according to the present invention for the simultaneous fabrication of identical blades.
Figure 45:
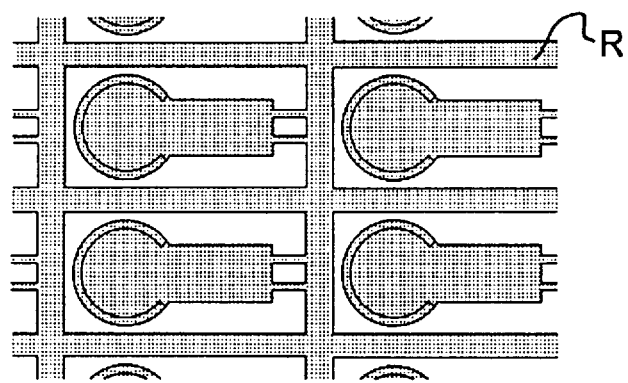

Using known processes, the wafer surface 12 is covered with an etchant masking layer 14 (FIG. 1) of silicon dioxide (or silicon nitride and silicon dioxide) which is photolithographically patterned (by means of a photomask and a photoresist layer, not illustrated) to provide (FIGS. 2 and 3) an etch mask 14 with a side edge 14a. The silicon surface is then etched downwardly and isotropically around the mask 14 to provide a surface 12a shown in profile in FIG. 4. The depth of the etch can be varied, and typically is in the range of 20–300 microns. Of significance, as described hereinafter, the etched surface 12a (for each device being made on the wafer) is present along only the one edge 14a of the mask 14. As previously noted, a plurality of devices are preferably simultaneously fabricated. FIGS. 44 and 45 show examples of identical devices formed on a common wafer.

The etch mask 14 is then removed and replaced with another masking layer which is photolithographically patterned to provide (FIGS. 5 and 6) a narrow, elongated rectangular etch mask 15 having side edges 16a–d, with the side edge 16a approximately coinciding with the vertical edge 12b of the etched surface 12a, and the side edges 16b–d overlying the original surface 12. (Alternatively, the etch mask 14 is not removed, but repatterned to provide the new mask 15.) The dimensions of the mask 15 are a function of the blade being made, but typical dimensions are: length 5–30 millimeters, width 2–10 micrometers and a thickness or height of 0.2–1.5 micrometers. In FIG. 6, the side edges 16a and 16b of the mask are straight and extend parallel to the <112> direction on the block surfaces 12 and 12a and the mask side edges 16c and 16d are perpendicular to the mask edges 16a and 16b. (A variation of the mask is shown in FIG. 7. In FIG. 7, the mask edges 16a and 16b, while still extending generally parallel to the <112> direction, are provided with a saw-tooth or undulating shape. The effect of this variation is described hereinafter.)

Figure 5:
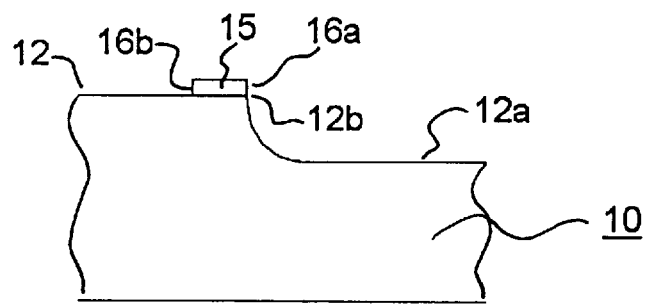
Figure 6:
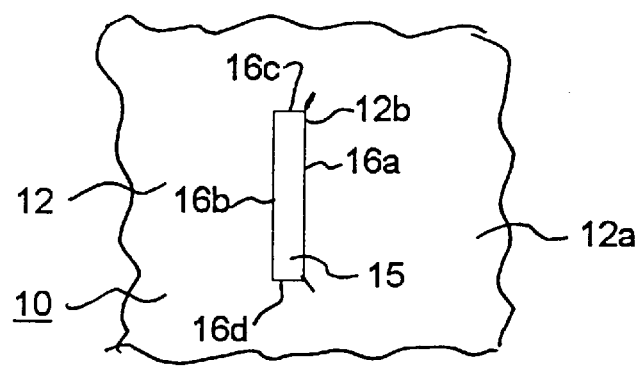
Figure 7:
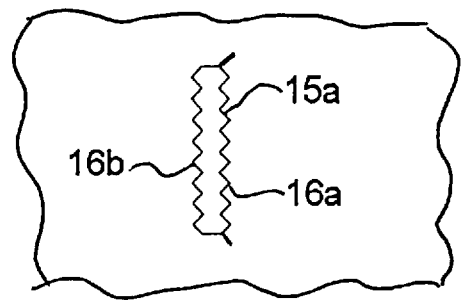
FIG. 7 is a view similar to FIG. 6 but showing a variation therefrom.

Although, as previously explained, technology disclosed in the a fore-cited U.S. patents is used according to the invention, the structure shown in FIGS. 5 and 6, comprising an etched surface 12a adjacent only to the mask edge 16a, is entirely unlike anything shown in the patents. A purpose and advantage of the FIG. 5 structure appears hereinafter.

The surfaces 12 and 12a adjoining the mask 15 are then etched to form (FIG. 9) an extending ridge 18 directly beneath the mask. Preferably, a two-step etching process is used, the first being a known anisotropic etching [such as Reactive Ion Etching (RIE) or KOH Solution] for forming (FIG. 8) an etched surface 12c adjoining the edges 16b–d of the mask 15. An advantage of such first step is that, while all the surfaces surrounding the mask 15 are etched downwardly relative to the mask edges to begin the formation of the pedestal (identified as 18a in FIG. 8), the height of the beginning pedestal 18a can be selected as desired while not reducing the width of the pedestal. This allows greater design flexibility in the height and shape of the completed blade. The amount of anisotropic etching (corresponding to the height of the vertical wall 17 formed directly beneath the mask edges 16b–d) is typically between 1–10 micrometers. Because the surface 12a (FIG. 5) is also etched during the anisotropic etching, the reference numeral 12d is used in FIG. 8 for the etched surface adjoining the edge 16a of the mask 15.

Figure 8:
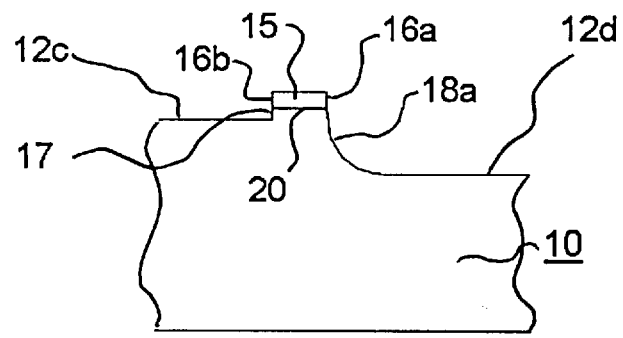
Figure 9:
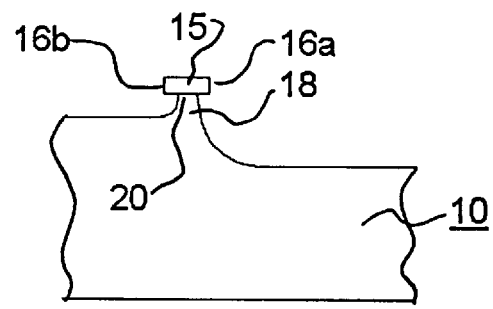

For providing an elongated ridge having a sharp apex, it is preferable, in accordance with the technology disclosed in the afore-cited patents, that the side walls of the ridge 18 converge inwardly towards the top of the ridge. To this end, the workpiece shown in FIG. 8 is isotropically etched (FIG. 9) using a "dry" process (RIE) or a "wet" process (KOH Solution) for both extending the height of the ridge 18 and for undercutting the edges 16a and 16b of the ridge for providing the desired convergence of the ridge side walls at the ridge top.

Figure 10:
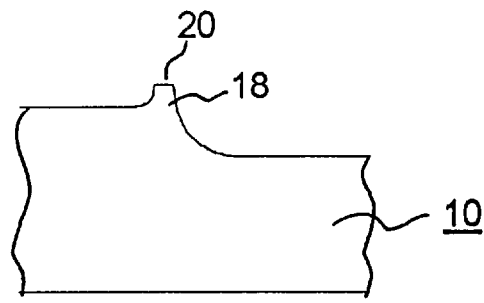
Figure 11:
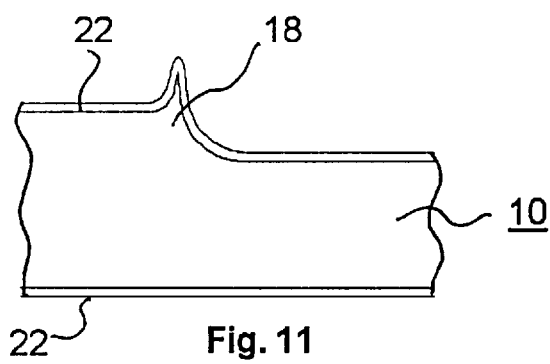

Preferably, as explained in U.S. Pat. No. 5,201,992, the isotropic etching is terminated before the ridge side walls intersect because a ridge apex formed by such intersecting sides is relatively rounded and blunt. For example, starting with a ridge having a flat top 20 (FIG. 8) having a width of 2–10 micrometers (corresponding to the width of the mask 15), the width of the ridge top 20 (FIG. 9) is reduced, during isotropic etching, to around 0.1–1.0 micrometers. The mask 15 is then stripped (FIG. 10) from the ridge 18 and the ridge top 20 is sharpened using an oxide forming and oxide stripping processing sequence such as that described in U.S. Pat. No. 5,201,992. For example, the workpiece is heated in dry oxygen at a temperature around 950° C. to form an oxide layer 22 (FIG. 11) covering all exposed silicon surfaces including the ridge, and the oxide layer is then etched away in concentrated hydrofluoric acid solution. The oxide forming-oxide stripping sequence can be performed a number of times. Each oxidation brings the two sides of the ridge closer together with increasingly smaller angle until they meet at an "atomically sharp" edge. Additional oxidation has no effect on the final edge configuration.

Figure 12:
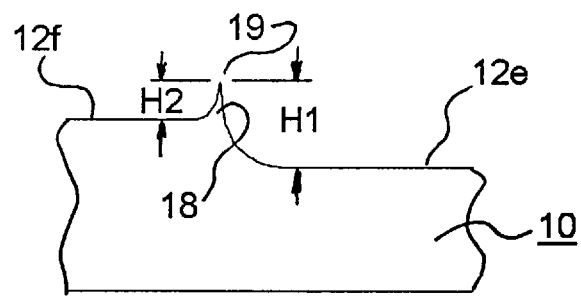

FIG. 12 shows a pointed ridge 18 resulting after the oxide layer 22 formed in a final oxidizing-sharpening process (FIG. 11) has been removed. At this stage of fabrication, a uniquely shaped structure has been provided comprising an elongated ridge having an atomically sharp edge, but wherein the height of the ridge with respect to adjoining surfaces varies from side to side of the ridge. The height H1 between the apex 19 of the ridge and the adjoining flat surface (now identified by reference numeral 12e) can be, for example, in the range of 20 to 300 micrometers; the height H2 can be, for example, in the range of 5–50 micrometers. The reason for this unique structure is described hereinafter.

Figure 13:
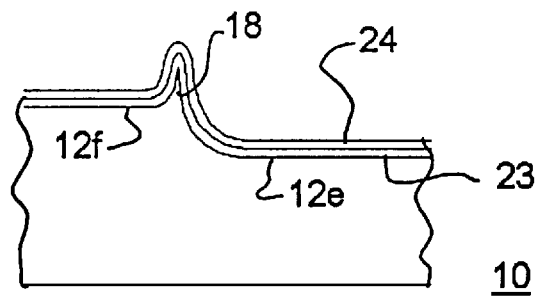

In a next processing step, an etchant masking layer is reapplied to the workpiece. An unusually deep silicon etch is to be performed, and, to this end, a very thin (20 nm) oxide layer 23 (FIG. 13) is thermally grown on the silicon surfaces 12e, 12f and the ridge 18, and a layer 24 of silicon nitride, of around 100–200 nm thickness, is deposited on the oxide layer 23. Silicon nitride provides improved etch masking while silicon oxide provides better adherence to the silicon surface. The two layers 23 and 24 are then patterned to provide an etchant mask as shown in FIGS. 14 and 15.

As previously noted, it is preferable to simultaneously fabricate a plurality of knife blades on a common substrate. To the stage of fabrication now reached, the processing of all the blades has been identical and all the blades are simply spaced apart over the surface of the wafer. At this point, however, it is convenient to fabricate structure on the wafer whereby the various blades can be eventually separated from one another.

Figure 14:
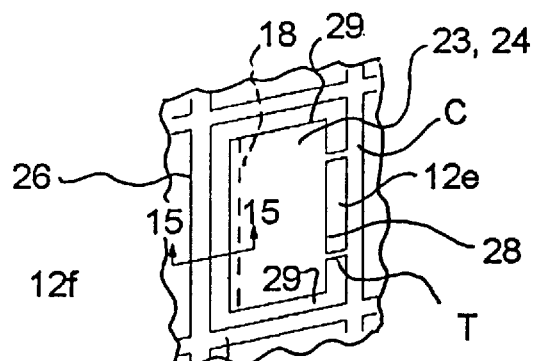
FIG. 14 is a plan views of a portion of a semiconductor workpiece illustrating a processing step performed after the step illustrated in FIG. 13.
Figure 15:
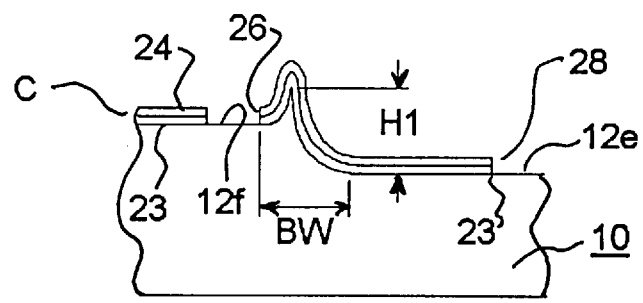

FIG. 14 is a plan view of a single blade workpiece but additionally shows a surrounding portion of the wafer surface which is patterned by the masking layers 23, 24 into a grid-like frame of intersecting strips R (rows) and C (columns). FIG. 15 is a cross-section taken along line 15—15 of FIG. 14 and shows the workpiece shown in FIG. 13 after the patterning of the masking layers 23, 24.

Considering, first, the blade workpiece (the central portion of FIG. 14), the edges 26 and 28 of the mask 23, 24 extend parallel to the ridge 18, with the mask edge 26 being disposed quite close to the ridge 18 and the edge 28 being disposed some convenient, larger distance from the ridge. For example, with a ridge 18 having a height H1 (relative to the surface 12e) of 50 micrometers and a base width BW of 5 micrometers, the spacings of the mask edges 26 and 28 from a vertical mid-plane of the ridge 18 are about 2 micrometers and between 1–10 millimeters, respectively. The small spacing of the edge 26 from the ridge is important, while the larger spacing of the edge 28 is less important and dependent upon how the blade is to be used. Because the original mask 15 (FIG. 6) used to form the ridge 18 was aligned with the mask edges 16a and 16b parallel to a <112> direction, both the ridge 18 and the mask edges 26 and 28 (FIG. 15) extend parallel to the same <112> direction. Also, the mask edges 29 (FIG. 14) and rows R extend parallel to a <112> direction of the wafer surface and make an angle of 109.5 degrees with mask edges 26 and 18.

Figure 16:
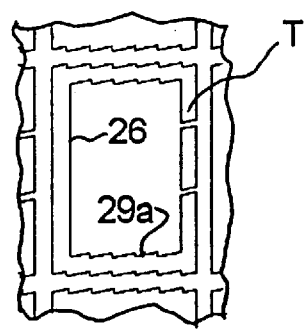
FIG. 16 is similar to FIG. 14 but showing a variation therefrom.

FIG. 16 shows a variation of the masking layer pattern shown in FIG. 14. In FIG. 16, the mask "horizontal" edges (as illustrated) are normally perpendicular to the mask "vertical" edges, but are not straight, as in FIG. 14, but have a sawtooth shape, i.e., the edges comprise a series of side by side triangular wedges with the sides 29a of the wedges being parallel to two different directions of the type <112>, i.e., each wedge side 29a corresponds to the intersection of a vertical {111} plane with the wafer surface. With this "sawtooth" geometry, the overall shape of the microtome knife (as seen from the top) can be kept nominally rectangular, with vertical walls etched through the wafer both at mask edges 26 and 29.

The silicon wafer is then anisotropically etched entirely through the thickness of the wafer using known anisotropic etches such as aqueous potassium hydroxide, ethylenediamine or tetramethylammonium hydroxide.

A plan view of the resulting workpiece appears exactly as shown in FIG. 14 or 16 except that substantially all of the wafer surface portions identified by numerals 12e and 12f have been etched away. The only portions remaining of the original wafer are those portions underlying the patterned masking layers 23, 24. The workpiece is now (see, also, FIG. 44) a filigree of spaced apart blade workpieces connected only by short tabs T to a grid-like frame R,C. The tabs T, for example, have a width of 10–100 micrometers. The frame row and column strips have a width of 0.1 to 1.0 mm. The various edges 26, 28 and 29 of the blade workpieces are spaced from the frame strips by between 0.5–1.0 mm.

Figure 17:
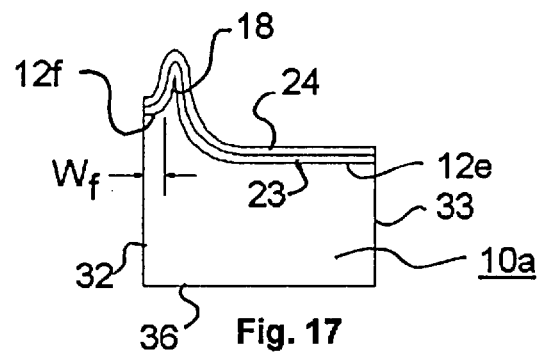
Figure 18:
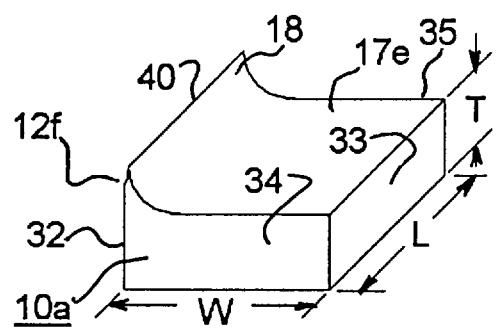
FIG. 18 is a perspective view of a knife blade according to the invention.

A cross-section of the blade workpiece appears as shown in FIG. 17 (See also FIG. 18). Owing to the described alignments of the mask edges 26, 28 and 29 with the crystal directions, anisotropic etching results in a generally rectangular block 10a having pairs of flat parallel surfaces 32,33 and 34,35 perpendicular to the top (as illustrated) surfaces 12e and 12f and the bottom surface 36. The top and bottom surfaces are not actually rectangles, but rhomboids with the side surface 34 forming an angle of 109.5 degrees with the side surface 32, as shown in FIG. 14.

The side surfaces 32 and 33 extend parallel to the ridge 18, and all the side surfaces 32–35 lie in the {111} set of planes.

The masking layers 23 and 24 are then removed and the workpiece appears as shown in FIG. 18 with the tabs not shown for clarity. (See, also, FIG. 44.) The workpiece includes a ridge 18 extending upwardly from one surface 12e of the block and closely adjacent to a block surface 32 intersecting the surface 12f. The apex 40 of the ridge is exceptionally sharp. This is further discussed hereinafter. By way of example, the block 10a has a length L of between 5–30 mm, a thickness Th of 0.5 mm and a width W of 2.0 mm. The width $W_f$ (FIG. 17) of the flat surface 12f extending between the side surface 32 and the base edge of the ridge 18 is about 2 micrometers and, in comparison with the other dimensions of the block, is so small that the ridge 18 is essentially an extension of the surface 32. The importance of this is discussed hereinafter.

Figure 19:
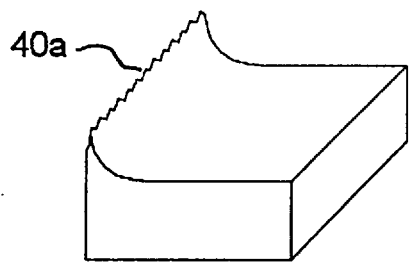
FIG. 19 is similar to FIG. 18 but showing a variation of the blade cutting edge resulting from using the etchant mask shown in FIG. 7.

FIG. 18 shows a straight cutting edge 40. However, if an etchant mask 15a (FIG. 7) is used having undulating side edges 16a, the resulting cutting edge 40a (FIG. 19) is serrated. This occurs because of variations in the thickness of the ridge resulting from the undulating mask edges. During sharpening, by successive oxide forming and oxide stripping sequences, the thickness of the ridge 18 (FIG. 11) is progressively reduced until the side walls along the full length of the ridge intersect to form a sharp apex. Such intersection occurs first where the ridge top surface 20 is most narrow. During further sharpening and further narrowing of the ridge, the ridge apex is lowered. The amount of reduction of height is a function of the mask width from point to point along the mask, i.e., upon the pattern of undulations of the mask side edges.

As mentioned, the present invention makes use of known technology, including a known process of providing an extending ridge having an exceptionally sharp apex. The structures described in the afore-cited U.S. patents are not described as having utility as knife blades and, indeed, an element of the present invention is the recognition that certain novel structures, relatively easily made using known semiconductor processing techniques, have utility as knife blades.

For example, a need exists for instruments, known as microtomes, for slicing thin layers of biological tissue. Elongated, ultra-sharp blades are required. Typical microtome blades, e.g., of glass, diamond, sapphire or stainless steel, have typical cutting surfaces, e.g. oppositely disposed flat surfaces tapering smoothly inwardly to a sharp edge, i.e., a wedge.

The blade shown in FIG. 18, however, differs from typical blades in that one of the blade surfaces, i.e., the surface 12e, is perpendicular to the plane of the cutting wedge. Such a blade has utility in, for example, microtome instruments.

Figure 20:
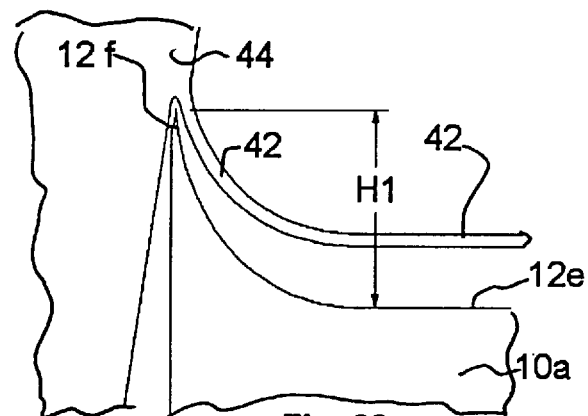
FIG. 20 is side view of the blade shown in FIG. 18 in use as a microtome.

In use in a microtome, the blade 10a is mounted in a suitable holder and used, as shown in FIG. 20, for cutting a thin layer 42 from a tissue body 44. Owing to the thinness, e.g., 10–100 nm, of the tissue layer 42, and its attendant flexibility, the layer 42 flows smoothly along the surface 12e without rupture. Accordingly, a useful blade is provided.

A common practice in the use of microtome blades is the provision of a thin film of water on one side of a blade cutting surface on which the freshly cut thin layer floats for easy removal. In use, as illustrated in FIG. 20, a film of water is present on the surface 12e, and for providing space for an adequately thick film of water, the height H1 of the ridge above the surface 12e is preferably in excess of 20 microns. This is a relatively large height, and well in excess of the height of the cones and ridges provided as disclosed in the afore-cited patents. Such large height is obtained by the processes hereinbefore described resulting (e.g., FIG. 12) in a ridge 18 having different heights with respect to its adjoining surfaces. By making H1 large (while H2 remains small), a ridge 18 having a large height is provided while still having a relatively large thickness owing to the presence of the surface 12f slightly below the cutting edge (see, also, FIG. 21). Such enlarged thickness adds strength to the cutting wedge.

The blade shape shown in FIG. 18 provides, in some uses, a special advantage. Some surgical (non-microtome) operations, for example, require a scalpel structure permitting the knife blade to be inserted to a chosen depth but not beyond. The height H1 of the ridge 18 (FIG. 20) above the block surface 12e is selected and varied from blade to blade, depending upon the desired depth of cut. In use, the ridge 18 is pressed into a body being cut until the surface 12e impacts against the body, the depth of the cut thus automatically corresponding to the height H1.

Blades made according to the present invention can have cutting edges significantly sharper than heretofore available. Photomicrographs of stainless steel blade edges, for example, show the blade edges with a radius of curvature of approximately 100 nm. Conversely, in comparable photomicrographs, the edges of blades made as herein disclosed appear with a radius of curvature of 0.5 nm. Also, while the surfaces adjacent to the cutting edge appear rough on both stainless steel and glass knives at low magnification (5,000×), the corresponding surfaces of the inventive blades are much smoother even at high magnifications (100,000×). Thus, exceptionally sharp blade edges are made possible according to the invention.

It is important to note that the method for oxidation sharpening assures that all blade edges are at the same degree of sharpness. It is commonly found that a semiconductor processing step such as the isotropic etch for forming ridge 18 (FIG. 9) is not uniform across a wafer, and that the width of the ridge may vary from blade to blade along the wafer surface. The parts of the wafer with the narrower ridges will necessarily form atomically-sharp edges before other parts of the wafer with wider ridges. By repeating the oxidation and oxide strip steps, all parts of the wafer will eventually form atomically sharp edges; and while the heights H1 and H2 (FIG. 12) in regions that originally contained narrow ridges will be less than the corresponding heights in regions that contained wider ridges, all the ridges will contain blade edges 19 of the same degree of sharpness. Thus the quality of the knife edges, measured in terms of uniformity of sharpness, is exceptional.

The exceptionally sharp blade edges made possible according to the invention are obviously relatively fragile. Therefore, in many applications, it is preferable to at least slightly dull the edges (or to make them less than maximally sharp) and, depending upon the knife application, strengthening the edges by the addition of one or more protective layers.

Figure 21:
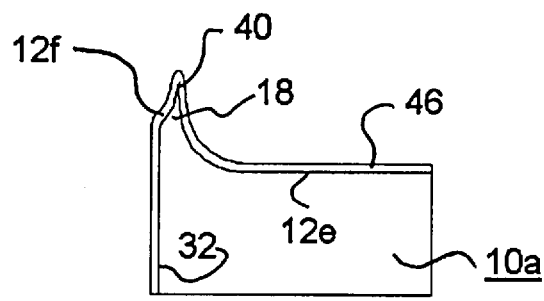
Figure 22:
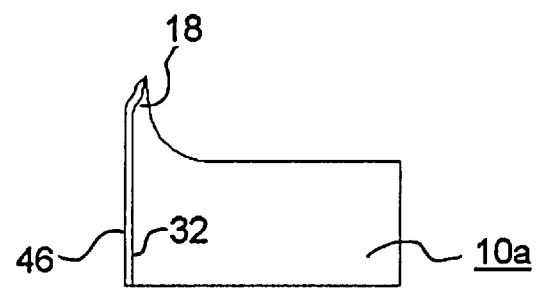

Thus, starting with an excessively sharp edge, e.g., having a radius of curvature of around 0.5 nm, it is possible to slightly dull the edge, e.g., to a radius of curvature of 1–50 nm, by etching, e.g., briefly immersing the workpiece in an etchant bath, or by controlled oxidation at a temperature above 1,100° C. Additionally, as shown in FIG. 21, the ridge 18, and the surfaces 12e, 12f and 32 adjoining the ridge, can be coated with a thin layer 46 of hard material (hardness greater than 1500 kg/mm$^2$) which not only increases the radius of curvature of the edge 40 (depending upon the thickness of the layer 46), but serves to strengthen and protect the ridge 18 and the cutting edge 40. Alternatively, the layer 46 can be deposited only on one surface of the ridge 18 as shown in FIG. 22. Such partial coating maintains a smaller radius of curvature at the edge than would be obtained with complete coverage (as shown in FIG. 21), and maintains sharpness for a longer time than is the case with no coverage. Sharpness is maintained because the less hard surface at the knife edge (silicon) wears away preferentially, maintaining the sharpness of the edge provided by the harder remaining material.

The layer 46 can comprise a thin (e.g., 2–50 nm) film of silicon dioxide thermally grown (e.g., in dry oxygen at a temperature in excess of 1075° C.) on the workpiece, or a layer (either directly on the silicon surfaces or overlying a previously applied layer of silicon dioxide) of a hard, smooth material such as silicon nitride, titanium diboride, diamond-like carbon or silicon carbide. Such materials can be deposited by known processes, e.g., by RF sputtering, and with thicknesses in the range of 2–100 nm.

At the conclusion of the blade processing steps (all performed while the blades are part of a single workpiece), the individual blades are separated by breaking the tabs T (FIGS. 14, 15 and 44). The tabs are easily broken in response to slight pressure.

In the blade illustrated in FIG. 18, the ridge 18 (terminating in the cutting edge 40) projects perpendicularly from an adjoining surface 12e (i.e., "vertically" from the flat surface 12e of the wafer). Processes are now described resulting in blades where the blade edge is located at the intersection of generally parallel but gradually inwardly tapering side surfaces (i.e., a blade edge extending generally "horizontally" in the plane of a wafer flat surface). One advantage of the "horizontal" blades is that curved blade edges can be readily made.

Figure 23:
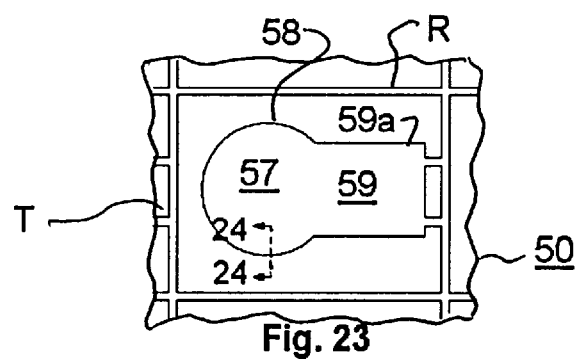
FIG. 23 is a plan view of a portion of a semiconductor workpiece for forming a knife blade in accordance with a second aspect of this invention.
Figure 24:
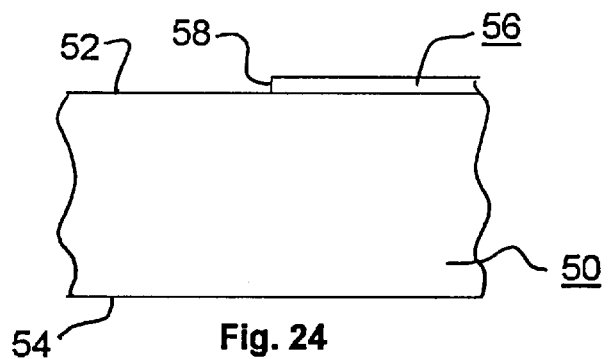
FIG. 24 is a cross-section of the blade workpiece taken along line 24—24 of FIG. 23.
Figure 25:
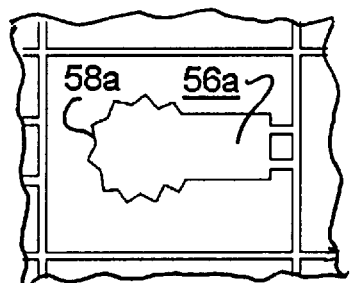
FIG. 25 is a view similar to FIG. 23 but showing a variation therefrom.

The starting workpiece (FIGS. 23 and 24) is a silicon wafer 50 having a pair of oppositely disposed, parallel top and bottom surfaces 52 and 54. An etched surface is to be cut entirely through the wafer and, to this end, an etchant masking layer, preferably of silicon carbide or boron nitride of 100–200 nm thickness, is grown on the top surface 52 and then patterned to provide an etchant mask 56 of predetermined shape (e.g., a semicircular portion 57 having a peripheral edge 58 joined to a rectangular portion 59 having a peripheral edge 59a). (FIG. 25 shows a mask 56a having an undulating mask edge 58a. This results in a blade, described hereinafter, having a serrated edge.)

Because the etchant mask 56 is to be used during etching entirely through the thickness of the wafer, as hereinafter described, the etchant mask 56 also defines a grid-like frame (FIG. 23) including column strips C, row strips R and tabs T.

The workpiece is then oxidized in known manner, e.g., in dry oxygen at 1,050° C. for 3 hours, for growing a layer 60 (FIG. 26) of silicon dioxide on the top surface 52 where it is not covered by the masking layer 56 and a silicon dioxide layer 62 completely covering the bottom surface 54. The oxide layers 60 and 62 preferably have a thickness of less than about 1 micron.

Figure 26:
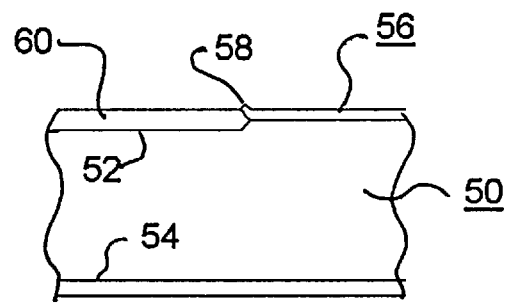
FIGS. 26 and 27 are cross-sectional views illustrating successive processing steps performed on the workpiece shown in FIGS. 23 and 24 (FIG. 26 also being a section taken along line 26—26 of FIG. 28)
Figure 27:
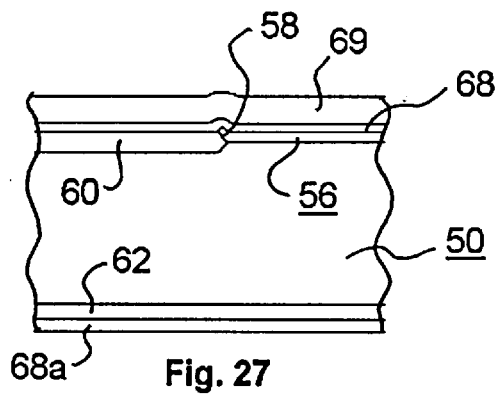

A second layer 68 (FIG. 27) of silicon carbide or boron nitride is grown over the masking layer 56 and the top oxide layer 60 and, simultaneously, a third layer 68a of the carbide or nitride is grown over the bottom oxide layer 62. The layer 68, but not the layer 68a, is then preferably covered with a "stiffening" layer 69, e.g., a polymer such as polyimide having a thickness around 5–10 mocrometers. The two upper layers 68 and 69 are then patterned (FIGS. 28 and 29) to provide a capping mask 70 overlying only the semicircular portion 57 of the underlying first etchant mask 56 but with a peripheral edge 72 extending beyond (e.g., 0.5 mm) and parallel to the edge 58 of the semicircular portion 57 of the etchant mask 56 and directly contacting the oxide layer 60. The capping mask 70 does not extend onto the rectangular portion 59 of the first etchant mask 56, nor onto the grid-like frame (R,C) also defined by the first etchant mask 56, hence sections taken through the workpiece shown in FIG. 28 along lines 26—26 still appear as shown in FIG. 26.

Figure 28:
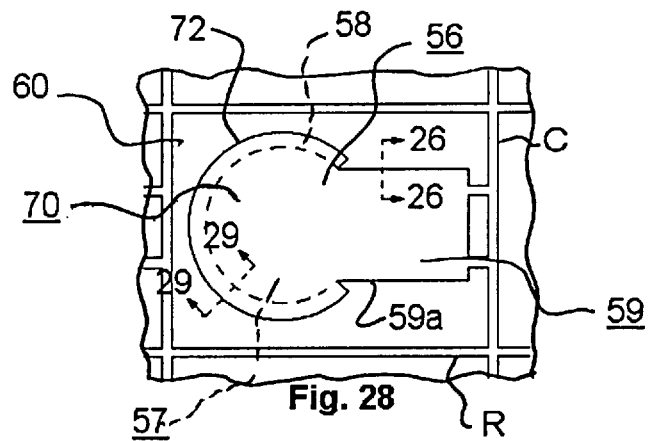
FIG. 28 is a view similar to FIG. 23 but at a still later stage in the fabrication process.
Figure 29:
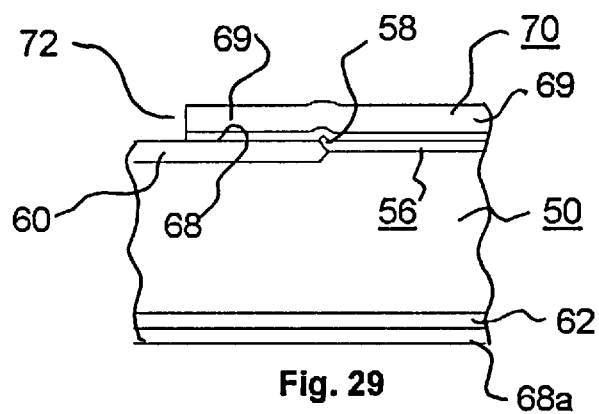
FIG. 29 is a cross-section taken along line 29—29 of FIG. 28.

A silicon oxide etchant, e.g., HF, is then used to remove the oxide layer underlying the layers 68 and 69. A ledge 76 (FIG. 30) of silicon carbide or boron nitride covered with the stiffening layer 69 is left extending over and spaced from a newly exposed surface 78 of the silicon wafer. The ledge 76 terminates in a semicircular edge 72. A plan view of the workpiece still appears as shown in FIG. 28. The etched surface 78 curves upwardly to join the original wafer surface 52 along a line 80 spaced inwardly from and parallel to the outer edge 72 of the ledge 76.

The "stiffening" layer 69 is used for adding physical strength to the cantilevered ledge 76. While not always essential, depending upon the particular blade being made, the "stiffening" layer 69 is generally desirable for increasing the reliability, i.e., the yield during manufacture of the process.

The original silicon surface 78 underlying the ledge 76 along with all other silicon surfaces exposed through the etchant mask 56 is then isotropically etched entirely through the wafer. The profile (slope from point to point in a vertical plane) of the various surfaces etched through the wafer is a function of the configuration of the overlying etchant mask.

Figure 31:
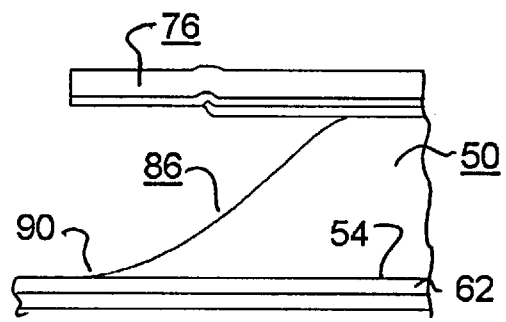

Beneath the cantilevered ledge 76, for example, an etched surface 86 (FIG. 31) is produced which has a relatively continuous slope and is essentially a flat surface. In FIG. 45, which shows a plurality of completed blades still attached by tabs T to the grid-like frame R,C, the etched surface 86 forms a semicircular (or C-shaped) cutting surface terminating in a cutting edge 90. In FIG. 31, the cutting edge 90 is shown at the intersection of the etched surface 86 and the wafer bottom surface 54.

Figure 32:
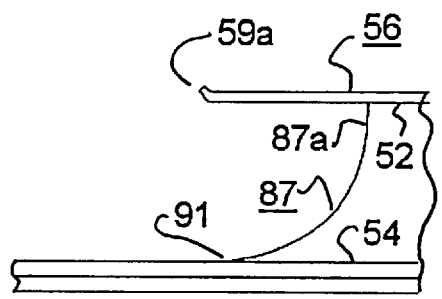
FIG. 32 is a view similar to FIG. 26 but at a later fabrication stage.

FIG. 32 shows an etched surface 87 formed beneath the edge 59a (FIG. 28) of the rectangular portion 59 of the first etchant mask 56. In comparison with the etched surface 86 (FIG. 31) formed beneath the cantilevered edge portion 76, the surface 87 has a generally circularly curved profile, including a surface portion 87a which is essentially perpendicular to the wafer surface 52. The circular etched surface results from the fact that, during isotropic etching, the etching proceeds at an equal rate, both laterally and downwardly. The equal lateral and downward etching occurs because the etchant fluid has access to the vertical wall formed directly beneath the mask as the horizontal surface adjoining the mask edge is etched downwardly.

Conversely, when the etching process begins with a cantilevered ledge 76 (FIG. 30) already in place, the restricted space beneath the mask ledge tends to retard circulation and replacement of spent etchant fluid within the restricted space. Accordingly, beneath the ledge 76, the rate of etching is slowed and the rate of slowing is a function of the length of the ledge. The greater the beginning length of the cantilevered ledge, the more gradual is the taper of the etched silicon surface 86.

As shown in FIGS. 31 and 32, both etched surfaces 86 and 87 intersect the wafer bottom surface 54 at highly acute angles along lines 90 and 91, respectively. While the edges formed by both lines 90 and 91 are relatively sharp, they are not atomically sharp because they have been produced solely by etching and not sharpened by an oxidizing-oxide stripping process.

Figure 33:
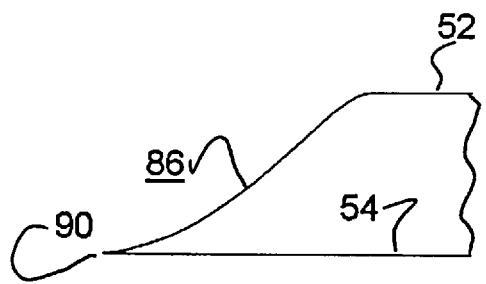

All the various masking layers are removed in oxygen plasma and HF solution and all edges are oxidation sharpened, as previously described (oxidation for a few hours at 950° C., oxide strip, repeat). The blade then appears as shown in FIG. 33, which shows a cross-section at the edge of the semicircular portion 57 (FIG. 28) of the blade. The edge 90, as well as the edge 91 (FIG. 32), are now atomically sharp.

Figure 34:
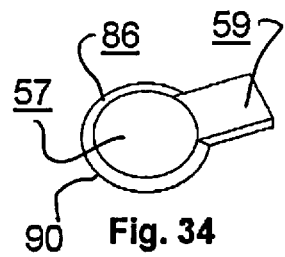
FIG. 34 is a perspective view of a first blade embodiment made according to the second aspect of this invention.
Figure 35:
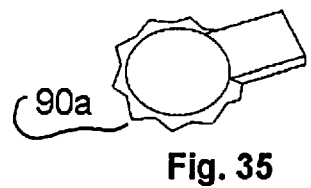
FIG. 35 is a view similar to FIG. 34 but showing the blade variation following from use of the etchant mask shown in FIG. 25.

The blade has been completed except for optional further processing, such as being coated with one or more protective coatings as previously described. A completed blade having a circular cutting edge 90 is shown in FIG. 34. (FIG. 35 shows a completed blade having a serrated or undulating circular edge 90a resulting from use of a mask 58a as shown in FIG. 25.) FIG. 45 shows a completed blade connected by tabs T to a grid-like frame. The blades are removed by breaking the tabs.

Figure 30:
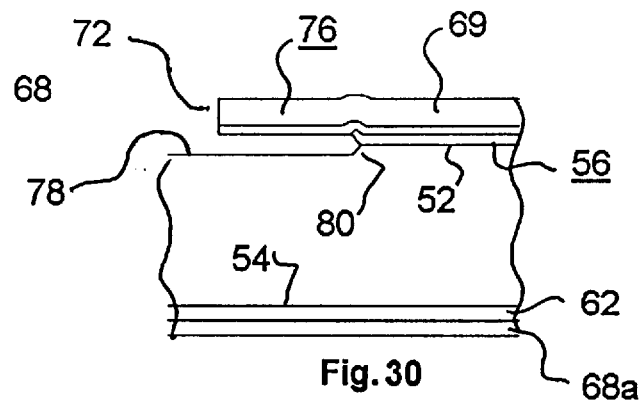
FIGS. 30, 31 and 33 are views similar to FIG. 29 but at later stages in the fabrication process.

Next described is a process for providing a blade generally similar to the blade shown in FIG. 34, but not using the external ledge approach illustrated in FIG. 30.

Figure 36:
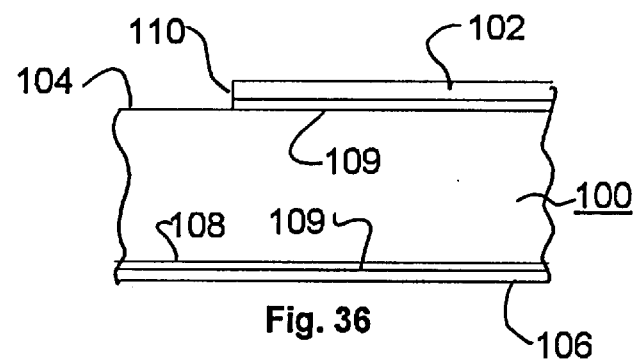
FIGS. 36, 39 and 42 are cross-sectional views illustrating the formation of a second blade embodiment according to the second aspect of this invention.
Figure 37:
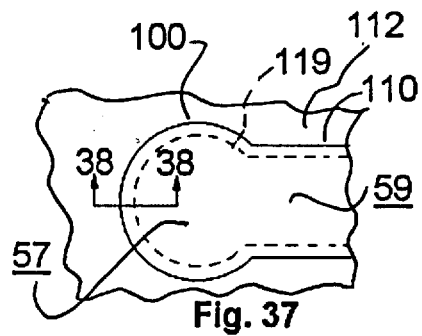
FIGS. 37 and 40 are plan views of a blade workpiece but at successive fabrication steps following that shown in FIG. 36.

The starting workpiece (FIG. 36) comprises a silicon wafer 100 having a patterned masking layer 102 on a top surface 104 thereof and a continuous masking layer 106 on a lower surface 108. Preferably, because extensive etching is to be performed, the masking layers 102 and 106 are of silicon carbide, boron nitride, platinum or palladium of around 120 nm thickness. Also, to improve the adherence of the platinum or palladium layers 102 and 106 to the silicon surfaces, a thin (20 nm) titanium layer 109 is preferably thermally grown on the silicon surfaces 104 and 108 prior to the deposition of the metal layers. The surfaces 104 and 108 can be parallel to any silicon crystal planes. The composite edge 110 of the masking layers 102, 109 is shaped (e.g., similarly as the edges 58 and 59a shown in FIG. 23) in accordance with the desired shape of the cutting edge in the completed blade. Then (FIGS. 37 and 38), the wafer is isotropically etched to provide a first etched surface 112. The etching depth is generally in the range 50–300 microns, depending on the desired final shape of the surface of the cutting edge.

Figure 38:
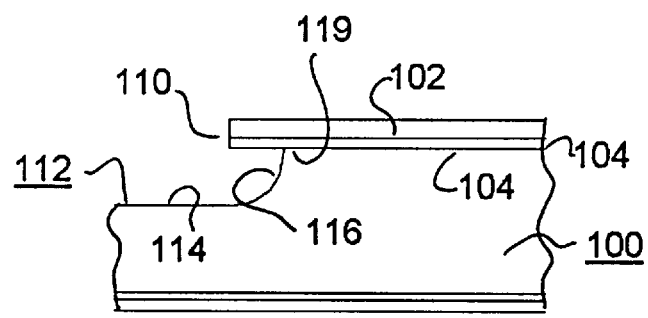
FIGS. 38 and 41 are cross-sections taken along lines 38—38 and 41—41, of FIGS. 37 and 40, respectively.
Figure 39:
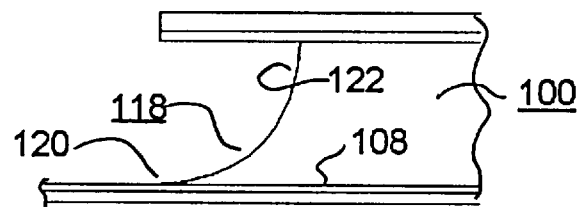

The etched surface 112 (FIG. 38) comprises a horizontal portion 114 joined to a circularly curved portion 116 which intercepts the original surface 102 along an edge 119. If the etching step illustrated in FIG. 38 were continued all the way through the silicon wafer, the resulting etched surface would appear as shown in FIG. 39. While a sharp edge 120 at the intercept of the etched surface 118 with the silicon lower surface 108 would be present, the etched portion 118 would include a wall portion 122 relatively closely spaced to the edge 120 and extending substantially perpendicular to the lower surface 108. While a blade having such a surface 118 adjoining the cutting edge 120 has utility, e.g., similarly as the blade illustrated in FIG. 20, a generally preferred blade shape is, as previously mentioned, a blade where the surfaces adjoining the cutting edge extend rearwardly thereof with relatively gradual tapers.

Figure 40:
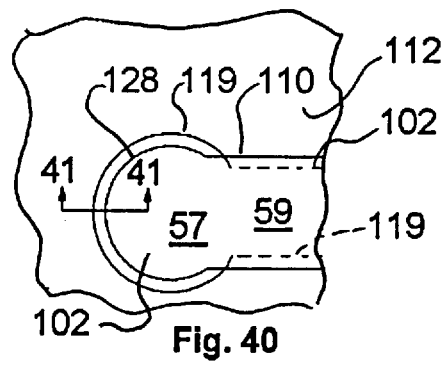

To achieve such gradual taper, the composite masking layer 102, 109 (FIG. 38) is further patterned to provide a composite edge 128 (FIGS. 40 and 41) extending along the periphery of the semicircular portion 57 of the blade workpiece and parallel to and spaced (e.g., 10–500 microns) from the intersection 119 of the previously etched surface 112 (FIG. 38) with the upper surface 104. The further patterning, i.e., the cutting back of the original edge 110 of the masking layer 102, 109 occurs only around the semicircular portion 57 of the mask and not along the rectangular portion 59.

A further isotropic etching process is performed (FIG. 42) for providing an etched surface 132 underlying the masking edge. The surface 132 extends entirely through the silicon wafer 100 and intersects the wafer lower surface 108 along a line 134 parallel to the original edge 110 (FIG. 36) of the masking layer 102, 109. Beneath the original edge 110 of the masking layer 102, 109 adjoining the rectangular portion 59 (FIG. 37) of the masking layer, the etched surface (118) is as shown in FIG. 39. With the formation of the etched surface 132, the basic configuration of the blade is established. Further processing steps, e.g., reducing the curvature of the blade edge 134 and providing one or more protective coating layers, either on one side only or on both sides of the blade surfaces, can be performed as previously described.

Figure 42:
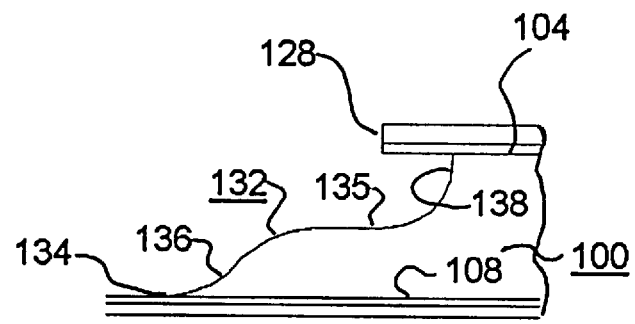

FIG. 42 shows the etched surface 132 including a horizontal portion 135 interconnecting two curved portions 136 and 138. Although the curved portion 138 curves sharpwardly upwardly, the vertical height of the portion 138 can be made relatively small (particularly in comparison with the height of the sharply rising wall 118 shown in FIG. 39), and the curved portion 138 is positioned relatively far from the cutting edge 134. Accordingly, in spite of the relatively sharp rise of the surface portion 138, the overall shape of the surface 132 adjoining the blade cutting edge corresponds, particularly in function, to a surface having a continuous and gradual rearward taper.

Figure 43:
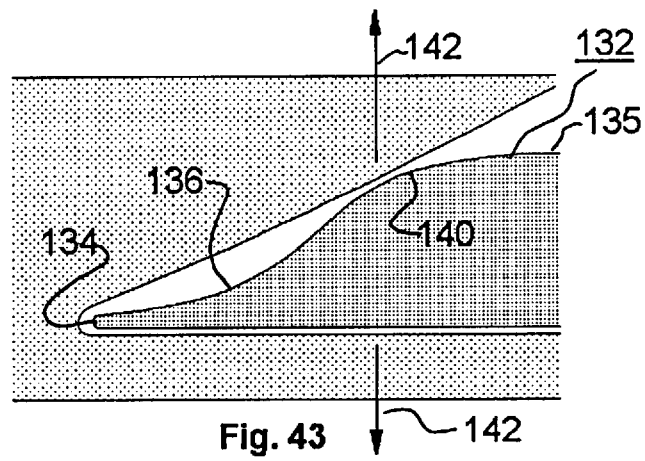
FIG. 43 is a view similar to FIG. 42 but on an enlarged scale and illustrating a use of the blade.

The curved portion 136 of the etched surface 132 immediately adjoining the edge 134 is shown on an enlarged scale in FIG. 43, where the blade is shown in use for cutting through a piece of material. Starting closely rearwardly of the blade edge 134, the surface 136 is generally concave until becoming convex along a surface portion 140 intersecting the horizontal portion 135 of the etched surface 132. Such concave blade surface 136 (corresponding, generally, to a "hollow ground" blade surface), terminating in a convex surface "bump" 140, is a desirable feature in that the bump 140 serves to add a tensile force, indicated by the arrows 142 in FIG. 43, to the material being cut. Such force decreases the local bond strength of the material in advance of the blade edge 134 and improves the cutting action of the blade. The position and dimensions of the bump 140 are a function of the shape of the etched surface 132 (FIG. 42), which is a function of the relative placement of the mask edges 110 and 128 (FIGS. 36 and 41, respectively), and the length of time of the two etching treatments. Accordingly, different configurations are obtainable.

FIG. 44 shows an array of formed blades 150 disposed on a common silicon wafer 152. Each blade 150 is formed as previously described in connection with FIGS. 1–18, but all the blades are simultaneously fabricated. In a last processing step, tabs T joining each blade to a supporting grid work of the wafer 152 are broken for separating all the blades from the wafer and from one another.

FIG. 45 is a view similar to that of FIG. 44 but wherein blades of the type shown in FIG. 34 are being made. The method of fabricating arrays of knives and removing the knives from the silicon wafers as shown in FIGS. 44 and 45 achieves the simultaneous fabrication of large numbers of knives at one time. This economical means of fabrication is a significant advantage provided by the invention.

Figure 46:
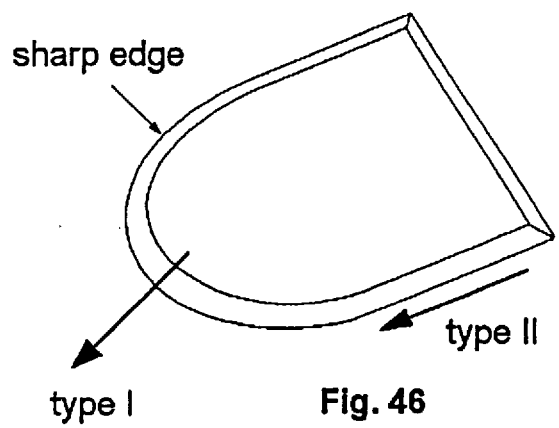
FIGS. 46 and 53 are perspective views of knife blades for illustrating uses thereof.

There are methods for automatically indicating a preselected depth of blade cut for two types of blade cutting motions. One type of cutting action (called type I) is where the blade moves in a direction normal (FIG. 46) to its cutting edge. The other type of motion (called "type II") is where the blade moves in a direction that has a large component of motion parallel to the cutting edge.

One method for automatically indicating a preselected depth of blade cut for type I action has been previously noted in connection with the blade shown in FIG. 18.

Figure 41:
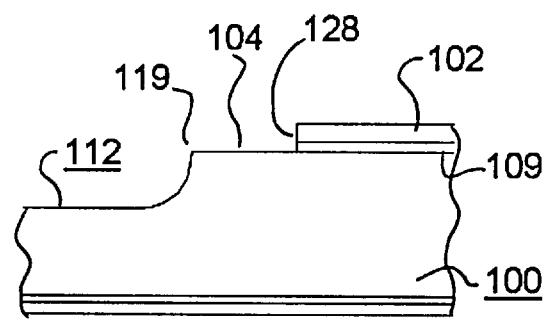
Figure 47:
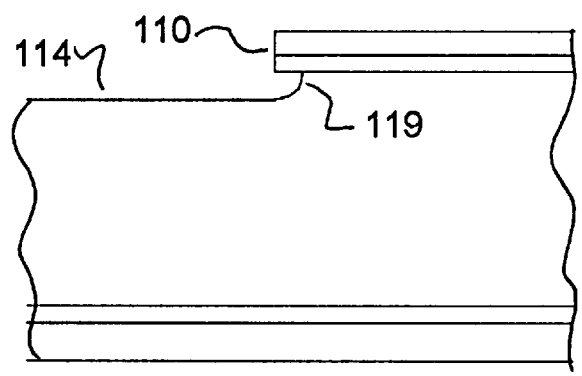
Figure 48:
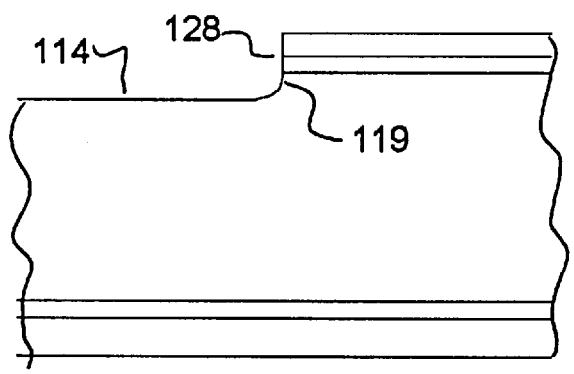
Figure 49:
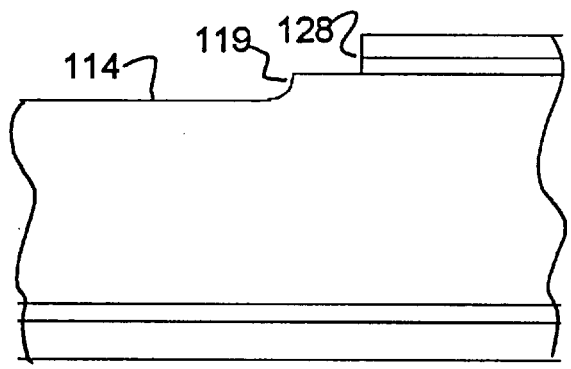
Figure 50:
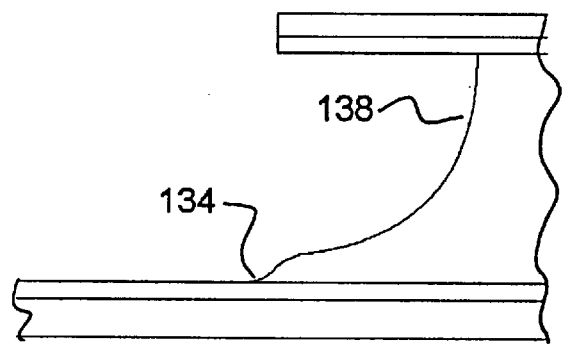
Figure 51:
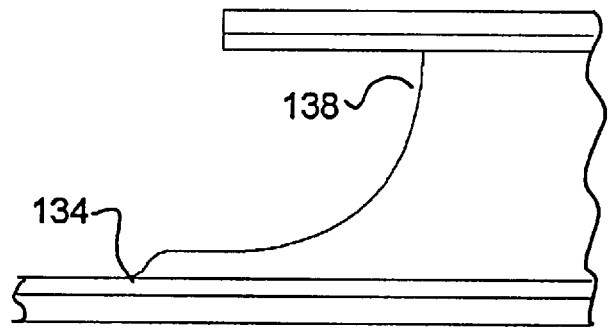

A second method for automatically indicating a preselected depth of blade cut for type I action is used in connection with the blade shown in FIG. 41 and involves adjustment of the relative positions of the mask edge 128 and the etched edge 119, and adjustment of the duration of the corresponding isotropic etches. The etch time used for forming surface 112 (FIG. 38) is short so that the vertical distance between surface 114 and the original surface 104 is small; see FIG. 47 in comparison with FIG. 48. Then, the subsequently formed mask edge 128 is positioned close to the edge 119. In FIG. 48, the edge 128 is coincident with edge 119, and in FIG. 49 the edge 128 is set back a short distance (say 30 microns) from edge 119. Then after etching entirely through the wafer, the resulting shapes are as shown in FIGS. 50 and 51, respectively. Wall 138 is steep in both cases because of the short etch time used to form surface 114 (FIGS. 47,48,49), and intersects the upper surface in a nearly perpendicular direction. In use, such perpendicular step offers some resistance to further penetration of the blade. The depth at which this resistance is encountered is preselected by adjustment of the position of the mask edge 128 with respect to the edge 119, and adjustment of the duration of the corresponding isotropic etches.

Figure 52:
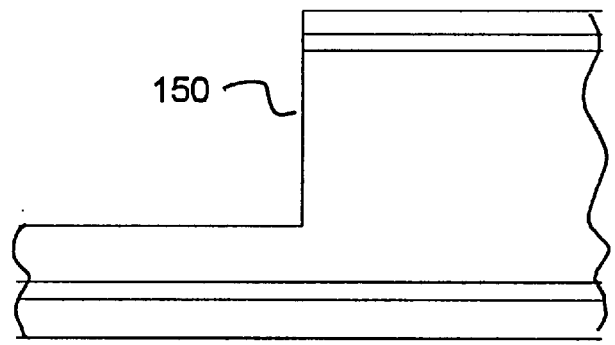
Figure 53:
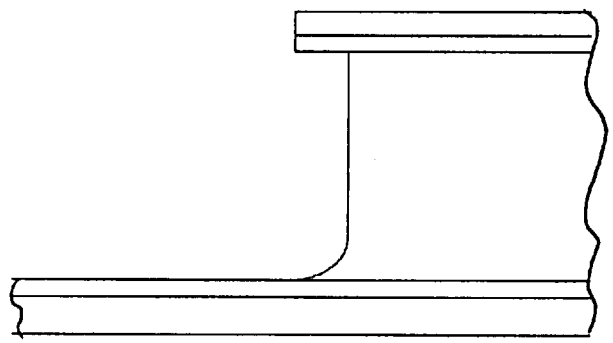

A third method for automatically indicating a preselected depth of blade cut for type I action replaces the first of two isotropic etches with an anisotropic etch. An anisotropic etch produces a vertical wall 150 (FIG. 52) instead of a curved surface 116 (FIG. 38). The anisotropic etching is made by applying known methods of Reactive Ion Etching (RIE) or wet chemical etching; the former is used where curved knife edges are needed, and the latter is used on {110} oriented wafers only for straight edges since the vertical wall 150 made by wet anisotropic etching necessarily lies on a {111} plane as described earlier. Blade structures (FIG. 53) made in this manner permit a preselected cutting depth that is shorter than the thickness of the wafer, and shorter than the preselected cutting depths obtained with blades that are produced by the method described in connection with FIGS. 50 and 51, where the preselected cutting depths are necessarily deeper than the wafer thickness.

Figure 54:
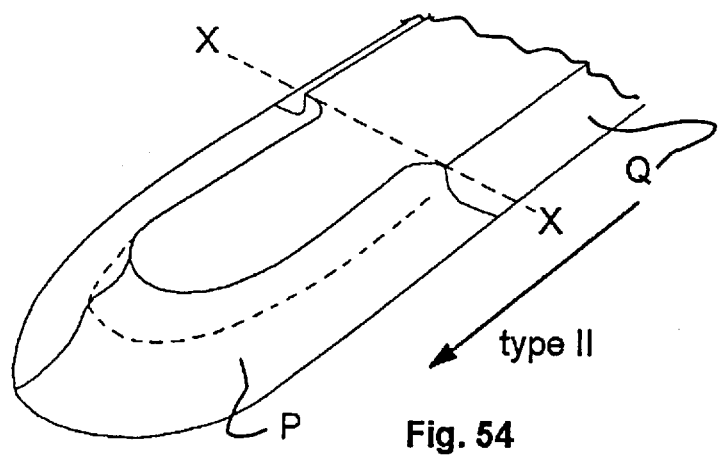

The method for automatically indicating a preselected depth of blade cut for type II action is to adjust the position of mask edge 128 (FIG. 41) with respect to edge 119 differently for different parts of the knife. For example, type II cutting action is assumed to be used with the knife shown in FIG. 54 in the direction shown to the depth X—X. For providing the desired shape in the region P. the edge 128 is set back from the edge 119 as shown in FIG. 41, giving a final profile as shown in FIG. 42. For providing the region Q, the edge 128 is made coincident with edge 119 giving a final profile as shown in FIG. 39. As the knife advances in the direction shown in FIG. 54, a new resistance to motion is added the knife penetrates to the distance X—X and the knife profile changes from that shown in FIG. 42 to that shown in FIG. 39.

What is claimed is:

1. A method of forming a knife blade comprising the steps of:

providing a first etchant masking layer covering a first surface of a substrate and a second masking layer partially covering a second surface of said substrate oppositely disposed to said first surface, said second masking layer having a shape terminating in a first edge exposing a portion of said second surface, etching into said substrate through said exposed portion of said second surface for forming a depression in said substrate, said depression having a bottom surface and a side surface connected to said second surface along a line, changing the shape of said second masking layer so that said changed second masking layer terminates in a second edge spaced from said line for exposing said depression and another portion of said second surface extending between said line and said second edge, and etching into said substrate through said depression and said another portion exposed by said changed second masking layer for forming a continuous surface extending between said substrate first and second surfaces, said continuous surface forming an acute angle with said first surface.

2. A method according to claim 1 including forming said continuous surface to form a substantially 90 degree angle with said second surface.

3. A method according to claim 1 wherein said continuous surface intersects said first surface along an extending edge, and including the step of forming said continuous surface to include differently contoured surface portions including a first portion adjoining said extending edge and having a concave contour and a second portion adjoining said first portion and spaced thereby from said extending edge and having a generally convex contour.

4. A method according to claim 3 including the step of forming said continuous surface to include a third portion adjoining said second portion, said third portion forming a substantially 90 degree angle with said second surface.

5. A method according to claim 1 wherein said continuous surface intersects said first surface along an extending edge having a first degree of sharpness, and including the steps of sharpening said extending edge to a second degree of sharpness greater than said first degree, and then blunting said extending edge for reducing the sharpness thereof to a third degree of sharpness intermediate said first and second degrees using a process selected from the group consisting of wet etching, dry etching and thermal oxidation.

6. A method according to claim 5 wherein said sharpening step comprises forming a layer of silicon dioxide on portions of said continuous surface and said first surface adjoining said extending edge and stripping away an oxide layer.

7. A method according to claim 5 wherein said process group additionally consists of coating one of said continuous surface and said first surface where said one surface adjoins said extending edge with a layer of material having a hardness greater than that of silicon.

8. A method according to claim 1 including the steps of simultaneously forming a plurality of identical knife blades by patterning a semiconductor wafer into a plurality of spaced apart individual knife blade workpieces, and performing an etching step for forming a plurality of spaced apart openings entirely through said wafer for forming a multi-apertured wafer frame, each of said openings substantially completely enclosing a knife blade workpiece connected to said frame by a tab.

9. A method of forming a knife blade comprising the steps of:

providing a first etchant masking layer covering a first surface of a substrate and a second masking layer partially covering a second surface of said substrate oppositely disposed to said first surface, said second masking layer terminating in a first edge exposing a portion of said second surface, etching into said substrate through said exposed portion of said second surface for forming a depression in said substrate, said depression having a bottom surface and a side surface connected to said second surface along a line, removing said second masking layer and replacing said second masking layer with a third masking layer partially covering said second surface and terminating in a second edge spaced from said line, said third masking layer exposing said depression and another portion of said second surface extending between said line and said second edge, and etching into said substrate through said depression and said another portion exposed by said third masking layer for forming a continuous surface extending between said substrate first and second surfaces, said continuous surface forming an acute angle with said first surface.

10. A method according to claim 9 wherein said continuous surface intersects said first surface along an extending edge, and including the step of forming said continuous surface to include differently contoured surface portions including a first portion adjoining said extending edge and having a concave contour and a second portion adjoining said first portion and spaced thereby from said extending edge and having a generally convex contour.

* * * * *